US00PP28986P2

(12) United States Plant Patent
O'Connell

(10) Patent No.: US PP28,986 P2
(45) Date of Patent: Feb. 20, 2018

(54) ***ECHEVERIA* PLANT NAMED 'AUTUMN FLAME'**

(50) Latin Name: *Echeveria hybrida*
Varietal Denomination: Autumn Flame

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 15/330,712

(22) Filed: Oct. 27, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct *Echeveria* cultivar named 'Autumn Flame' is disclosed, characterized by overlapping foliage forming rosettes. Foliage is uniquely shiny and mahogany in color. Plants grow unusually rapidly and exhibit tolerance for both heat and humidity. The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

2 Drawing Sheets

Latin name of the genus and species: *Echeveria hybrida.*
Variety denomination: 'AUTUMN FLAME'.

BACKGROUND OF THE INVENTION

The new cultivar, *Echeveria* 'Autumn Flame', is the product of a planned breeding program. The new variety originated from a cross pollination of the unpatented seed parent, *Echeveria* 'Doble Cabeza' with the pollen parent an unpatented, proprietary variety of *Echeveria* referred to as 'Color 07'. The cross pollination was made during April 2012 in Vista, Calif., at a commercial greenhouse. The new cultivar 'Autumn Flame' was discovered by the inventor, Renee O' Connell in September 2013, in Vista, Calif. at a commercial greenhouse.

Asexual reproduction of the new cultivar 'Autumn Flame' was first performed in Vista, Calif., at a commercial greenhouse, by terminal vegetative cuttings in September 2013. *Echeveria* 'Autumn Flame' has since produced multiple generations and has shown that the unique features of this cultivar are stable and reproduced true to type.

SUMMARY OF THE INVENTION

The cultivar 'Autumn Flame' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AUTUMN FLAME'. These characteristics in combination distinguish 'AUTUMN FLAME' as a new and distinct *Echeveria* cultivar:

1. Rich, mahogany color not seen in commonly in *Echeveria.*
2. Shiny, undulate foliage.

3. Unusual rosetting habit. Leaves arise from the plant center in an "overlapping" morphology; each leaf slightly overlaps the proximal leaf. Due to this overlapping of the leaves, as the plant grows and leaves appear one above another, the overall appearance is of a "spiralling" or "twirling" rosette.
4. Relatively rapid growth for an *Echeveria*, reducing production time.
5. Exhibited tolerance for combined heat and humidity.
6. Coloration suitable and complimentary for combination plantings.

PARENTAL COMPARISON

Plants of the new cultivar 'Autumn Flame' are similar in most horticultural characteristics to the seed parent variety. However, plants of the new cultivar 'Autumn Flame' differ in the following:

1. 'Autumn Flame' does not suffer the same vulnerability to *Fusarium echeveriae* exhibited by *Echeveria* 'Doble Cabeza'.
2. 'Autumn Flame' produces larger rosettes than *Echeveria* 'Dobie Cabeza', and without the tendency to bifurcate that *Echeveria* 'Doble Cabeza' exhibits.
3. 'Autumn Flame' exhibits leaves of mahogany with a satin texture, that do not exhibit the tendency towards physiological "edema" during certain times of the year, whereas the leaves of *Echeveria* 'Doble Cabeza' are thicker, less undulate, do not exhibit the "satin" texture, and can exhbit some tendency towards physiological "edema" during certain times of the year.
4. The leaf margins of 'Autumn Flame' are of lighter red than the overall mahogany leaf color, whereas the leaf margins of *Echeveria* 'Doble Cabeza' are the same color as the leaves.

Plants of the new cultivar 'Autumn Flame' can be compared to plants of the pollen parent, and are similar in most horticultural characteristics. However, plants of the new cultivar 'Autumn Flame' differ in the following:

1. 'Autumn Flame' has more undulate leaf margins than does *Echeveria* 'Color 07'.
2. *Echeveria* 'Color 07' exhibits matte textured, blue violet leaves, whereas *Echeveria* 'Autumn Flame' exhibits satin textured, mahogany colored leaves.
3. The rosette of 'Autumn Flame' tends to grow taller with time, whereas the rosette of *Echeveria* 'Color 07' tends to maintain the flatter morphology.
4. *Echeveria* 'Color 07' produces leaves that are more rounded apically, whereas the leaves of 'Autumn Flame' are longer, and mucronate at the apex of the leaf.

COMMERCIAL COMPARISON

The new cultivar 'Autumn Flame' can be compared to the unpatented commercial variety *Echeveria* 'Perle van Nurnburg'. Plants of the new cultivar 'Autumn Flame' differ in the following:

1. *Echeveria* 'Autumn Flame' exhibits rosettes of mahogany, whereas those of *Echeveria* 'Perle von Nurnberg' are a lilac-mauve color.
2. The leaves of *Echeveria* 'Autumn Flame' have a shiny texture, whereas the leaves of *Echeveria* 'Perle von Nurnberg' have a matte, glaucous texture.

The new cultivar 'Autumn Flame' can be compared to the unpatented commercial variety *Echeveria* 'Afterglow'. Plants of the new cultivar 'Autumn Flame' are similar to 'Afterglow' in most horticultural characteristics. However, plants of the new cultivar 'Autumn Flame' differ in the following:

1. 'Autumn Flame' produces leaves with a shiny, texture, whereas *Echeveria* 'Afterglow' produces matte, glaucous leaves.
2. 'Autumn Flame' has a warm mahogany colored rosette as compared to the blue and purple rosette of *Echeveria* 'Afterglow'.

BRIEF DESCRIPTION OF THE PHOTOGRAPHS

The accompanying photographs in FIG. 1 through FIG. 2 illustrate in full color typical plants of 'AUTUMN FLAME' grown in a greenhouse in Vista, Calif. Plants are both approximately 5 months from a rooted cutting. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500 to over 4000 foot-candles. Temperatures ranged from 10° C. to 38° C. night and day. No artificial light, photoperiodic treatments or chemical treatments were given to the plants.

DETAILED BOTANICAL DESCRIPTION

Figure 1:
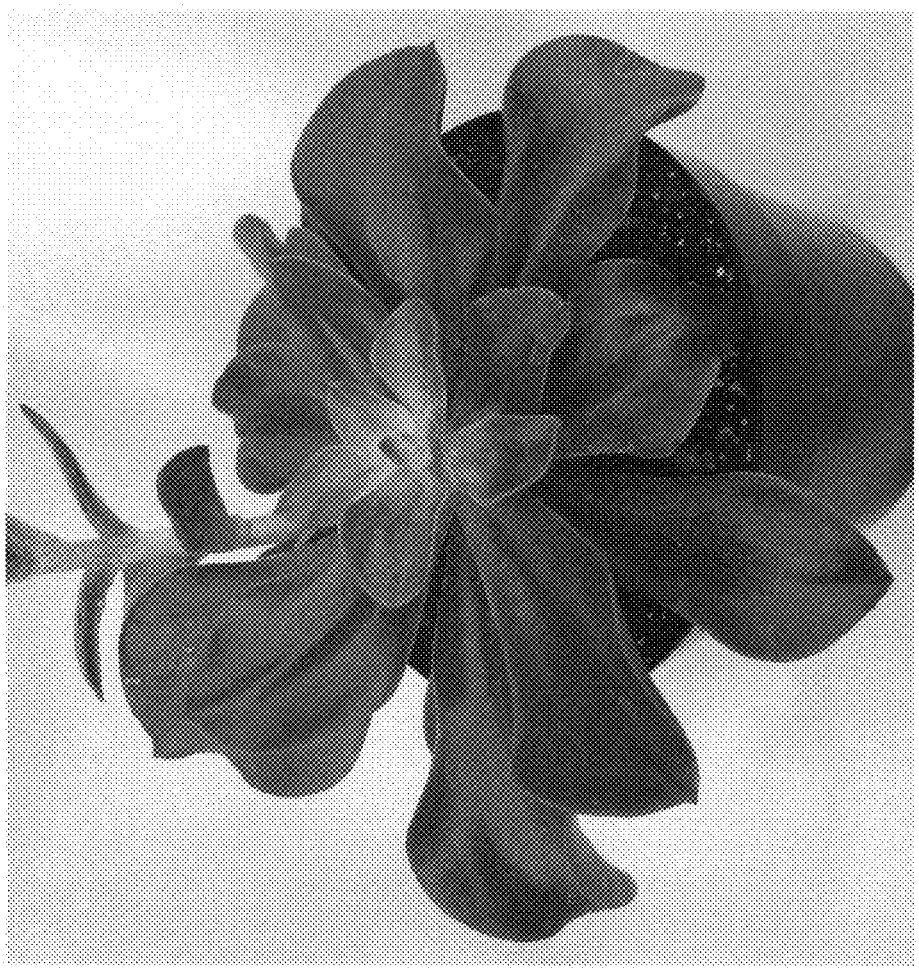
FIG. 1 illustrates in full color a typical of plant of *Echeveria* 'Autumn Flame' grown in a greenhouse in Vista, Calif. at approximately 2500 foot candles.
Figure 2:
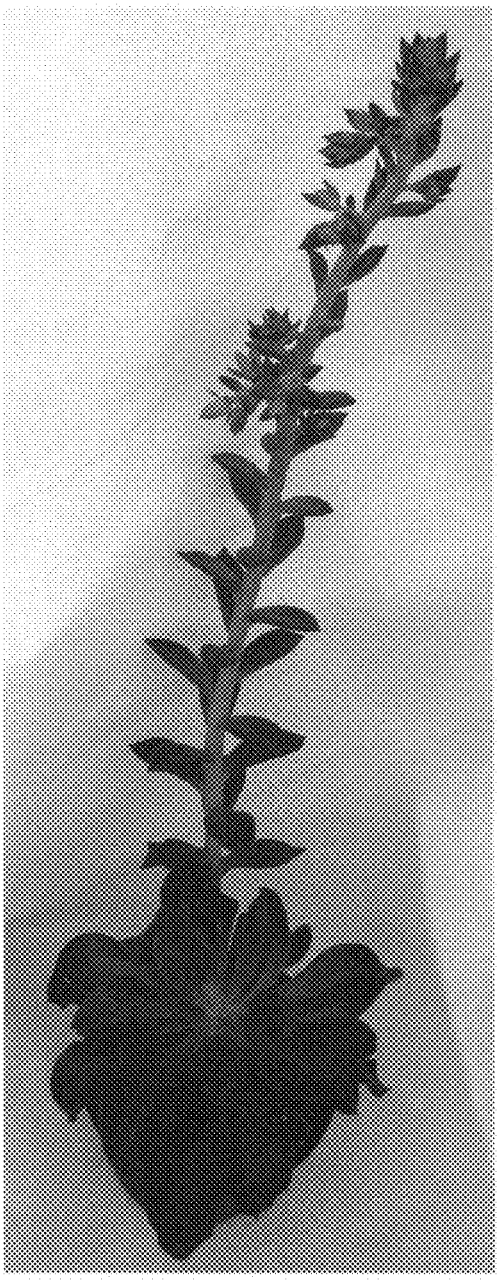
FIG. 2 illustrates in full color a typical of plant of *Echeveria* 'Autumn Flame' grown in a greenhouse in Vista, Calif. at approximately 4000 foot candles.

In the following description, color references are made to The Royal Horticultural Society Colour Chart, 2007 except where general terms of ordinary dictionary significance are used. The following observations and measurements describe 'Autumn Flame' plants in a commercial greenhouse in Vista, Calif. Temperatures ranged from approximately 10° C. to 38° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria hybrida* 'AUTUMN FLAME'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 10 cm.

Growth habit: Dense rosette.

Height: Approximately 5 cm to top of highest leaf. Approximately 30 cm to 50 cm to top of highest inflorescence.

Plant spread: Approximately 17.5 cm.

Growth rate: Rapid.

Branching characteristics: Not typically observed.

FOLIAGE

Leaf:

*Arrangement*.—Rosulate.

*Average length*.—Approximately 7.5 cm. Longest 11 cm.

*Average width*.—2.5 cm.

*Widest width*.—Approximately 5.0 cm.

*Width at base*.—Average 1.4 cm.

*Shape of blade*.—Spatulate.

*Apex*.—Irregularly obtuse, mucronate.

*Base*.—Broad attenuate.

*Margin*.—Entire.

*Aspect*.—Undulating.

*Texture of top surface*.—Glabrous.

*Texture of bottom surface*.—Glabrous.

*Appearance of top surface*.—Very shiny.

*Appearance of bottom surface*.—Matte.

*Quantity of leaves per plant*.—Average range 15 to 18.

*Color*.—Young foliage upper side, towards apex: Near RHS Greyed-Purple N187A, margin brightly colored between 185B and Red 45D. Young foliage upper side, mid-section: Near RHS Greyed-Purple N187A, margin brightly colored between 185B and Red 45D. Young foliage upper side, towards base of leaf: Base near Green 138B, towards mid-section flushed Greyed-Purple N187A. No difference in color of basal margin from color of leaf blade. Young foliage, under side, towards apex of leaf: Near RHS Greyed-Purple N187C, thickly covered with N186C. Flushed near margin 187C, thin marginal line 187D. Young foliage upper side, mid-section: Near RHS Greyed-Purple 187B, margin brightly colored between 185B and Red 45D. Young foliage, under side, towards base of leaf: Near RHS Green 138B. Margin 138C. Mature foliage upper side, towards apex of leaf: Near RHS Greyed-Purple N186B. Thin marginal color near 185B. Mature foliage upper side mid-section: Near RHS N187A. Thin marginal color near 185B. Mature foliage, upper side, towards base of leaf: Near RHS Green 138B, margin 138C. Mature foliage, under side, towards apex of leaf: Near Green 138B, completely and heavily flushed Greyed-Purple 187B. Very thin marginal coloration Red 46D. Mature foliage, under side, towards base of leaf: Near RHS Green 138B, 138C at lowest section. Margin 138C.

*Venation*.—There is no visual appearance of venation.

FLOWER

Natural flowering season: Spring through Summer.

Inflorescence type and habit: Erect, composed of several simple or bifurcate cincinni, each cincinnus typically with 3 to 5 flowers.

Rate of flower opening: About 5 days from bud stage to open flower.

Flower longevity on plant: 3-4 days, depending upon ambient temperatures.

Quantity of flowers: 30 to 50 individual flowers and buds.

*Total Inflorescence size*.—Height: Approximately 17 cm. Width: Approximately 8.0 cm.

*Corolla*.—Arrangement: Pentagonal, fused. Size: Length: Approximately 1.1 cm. Width: Approximately 0.7 cm at widest point. Lobe Length: Approximately 0.4 cm. Lobe width: Approximately 0.3 cm.

Petals:

*Margin*.—Entire.

*Shape*.—Unfused section deltate.

*Apex*.—Acute.

*Base*.—Fused, approximately ¾ entire length.

*Texture*.—Glabrous.

*Color*.—When opening: Petal color, outer surface: Near RHS Red 43C, slightly glaucous when immature, glaucous coloration near N187D. Inner petals not visible until fully opened. Fully opened: Outer surface: Near Red 45C, base Red 49A. Inner surface: Apex near Red 46B, center section in 46C, base 47D. Color Changes when Aging: All surfaces darken to Red 44A, apex flushed 187A.

Bud: (near opening):

*Shape*.—Conical.

*Length*.—Approximately 1.0 cm.

*Diameter*.—Approximately 0.6 cm.

*Color*.—Towards apex of bud: Near Red 50B, flushed N187C.

*Color, towards base of bud*.—Near Red 43B.

Sepals:

*Margin*.—Entire.

*Shape*.—Broad elliptic.

*Apex*.—Acute.

*Base*.—Truncate.

*Texture*.—Glabrous, upper and lower surfaces.

*Appearance*.—Moderately glossy upper and lower surfaces.

*Color*.—Outer: Near RHS N186C, base 186D. Inner: Near RHS 187A, base 186C.

Peduncle:

*Length*.—Average range 18 to 25 cm.

*Width*.—Approximately 1.0 cm.

*Strength*.—Strong.

*Texture*.—Glabrous.

*Color*.—Near RHS Red 50C.

Pedicels:

*Length*.—Approximately 0.5 cm

*Width*.—Approximately 0.3 cm.

*Strength*.—Strong, flexible.

*Texture*.—Glabrous.

*Color*.—Near RHS 186C, flushed Greyed-Red 181C.

*Fragrance*.—None detected.

REPRODUCTIVE ORGANS

Stamens: (Androecium).

*Number*.—Average 10.

*Filament length*.—Approximately 0.5 cm.

*Filament color*.—Near RHS White N155C.

*Anther length*.—0.1 cm.

*Anther color*.—Near RHS Yellow 12C.

*Anther shape*.—Oblong.

*Pollen color*.—Near RHS Yellow 12C.

Pistil: (Gynoecium).

*Number.—Average* 5.

*Length*.—Approximately 0.8 cm.

*Style color*.—Near White N155C.

*Stigma*.—Shape: Linear. Color: Near S RHS 187B. Ovary Color: Near RHS White 155C.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: More resistance to *Fusarium* than other dark *Echeveria* cultivars. Neither resistance or susceptibility to other normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'AUTUMN FLAME' as herein illustrated and described.

* * * * *